United States Patent
Assmann et al.

(10) Patent No.: US 6,455,488 B1
(45) Date of Patent: Sep. 24, 2002

(54) PROCESS OF MAKING ALKYL SULFATE GRANULATES

(75) Inventors: Georg Assmann, Juechen; Olaf Blochwitz, Genthin; Andreas Syldath; Ditmar Kischkel, both of Monheim, all of (DE)

(73) Assignee: Cognis Deutschland GmbH, Duesseldorf (DE)

(*) Notice: Subject to any disclaimer, the term of this patent is extended or adjusted under 35 U.S.C. 154(b) by 0 days.

(21) Appl. No.: 09/700,309

(22) PCT Filed: May 3, 1999

(86) PCT No.: PCT/EP99/02967

§ 371 (c)(1),
(2), (4) Date: Jan. 12, 2001

(87) PCT Pub. No.: WO99/58630

PCT Pub. Date: Nov. 18, 1999

(30) Foreign Application Priority Data

May 11, 1998 (DE) .......................................... 198 20 943

(51) Int. Cl.$^7$ ............................................... C11D 17/00
(52) U.S. Cl. ....................... 510/445; 510/446; 510/447; 510/426; 510/428
(58) Field of Search ................................ 510/446, 447, 510/445, 450, 426, 428

(56) References Cited

U.S. PATENT DOCUMENTS

| | | |
|---|---|---|
| 4,253,993 A | 3/1981 | Ramsey, III et al. |
| 5,516,447 A | 5/1996 | Bauer et al. |
| 5,668,100 A | 9/1997 | Schmid et al. |
| 5,824,633 A | 10/1998 | Kischkel et al. |

FOREIGN PATENT DOCUMENTS

| | | |
|---|---|---|
| DE | 44 25 968 | 2/1996 |
| DE | 197 50 424 | 5/1999 |
| EP | 0 603 207 | 6/1994 |
| EP | 0 665 288 | 8/1995 |
| WO | WO93/04162 | 3/1993 |
| WO | WO95/02036 | 1/1995 |
| WO | WO95/08616 | 3/1995 |
| WO | WO95/29981 | 11/1995 |
| WO | WO96/00611 | 1/1996 |

*Primary Examiner*—Necholus Ogden
(74) *Attorney, Agent, or Firm*—John E. Drach; Steven J. Trzaska

(57) ABSTRACT

A process for making substantially odorless granules of alkyl sulfates corresponding to formula (I): $R-O-SO_3X$ (I) wherein R is an alkyl group containing from 6 to 18 carbon atoms, and X is selected from the group consisting of an alkali metal, an alkaline earth metal, ammonium, an alkyl ammonium, and alkanolammonium, and a glucammonium ion, the process involving: (a) providing a water-containing paste of alkyl sulfates having a content of unsulfonated components of greater than 0.3% by weight; and (b) simultaneously granulating and drying, in a fluidized bed, the water-containing paste of alkyl sulfates to form substantially odorless granules of alkyl sulfates, and wherein the substantially odorles granules thus formed have less than 0.2% by weight, based on the weight of active substance, of unsulfonated components present therein.

9 Claims, No Drawings

PROCESS OF MAKING ALKYL SULFATE GRANULATES

BACKGROUND OF THE INVENTION

This invention relates to a process for the production of substantially odorless granules of alkyl sulfates and to their use for the production of laundry detergents, dishwashing detergents and cleaners and for the production of cleansing cosmetics.

Alkyl sulfates are conventional surfactants which are mostly used in detergents. In the method used for their production, they accumulate in the form of water-containing pastes with water contents of 35 to 65% by weight. In order to obtain solid free-flowing products, the water-containing pastes are dried, for example in a spray drying tower, to form spray-dried powders which, unfortunately, only have a low bulk density. An alternative to spray drying is granulation, more particularly in a fluidized bed. For example, it is known from European patent EP-B-603 207 that water-containing pastes of alkyl sulfates can be converted into granules of high bulk density by granulation and simultaneous drying in a continuous fluidized bed. It is also possible by this process to incorporate inorganic or organic carrier materials.

Accordingly, although it is known in principle that granules can be produced from water-containing pastes of alkyl sulfates, the problem posed by the unpleasant odor of water-containing alkyl sulfate pastes and spraydried powders or granules thereof remains unsolved. This unpleasant odor occurs above all with alkyl sulfates which contain 8 to 14 carbon atoms in the alkyl moeity. On account of their unpleasant odor, alkyl sulfates such as these have hitherto only been used in small quantities in cosmetics and, even then, have been heavily perfumed.

The problem addressed by the present invention was to provide free-flowing, dust-free and, above all, substantially odorless alkyl sulfates.

The problem stated above has surprisingly been solved by granulating and, at the same time, drying conventionally obtainable water-containing alkyl sulfate pastes in a fluidized bed until the content of unsulfonated components in the granules has fallen below 0.2% by weight, based on active substance content.

BRIEF SUMMARY OF THE INVENTION

Accordingly, the present invention relates to substantially odorless granules of alkyl sulfates corresponding to formula (I):

$$R-O-SO_3X \quad (I)$$

in which R is an alkyl group containing 6 to 18 carbon atoms and

X is an alkali metal, alkaline earth metal, ammonium, alkyl ammonium, alkanolammonium or glucammonium ion, with a content of unsulfonated components of less than 0.2% by weight, based on active substance content.

The substituent R in formula (I) is derived from alcohols with the formula ROH, where R is as defined above. Accordingly, R may be derived from the alcohols, such as caproic alcohol, caprylic alcohol, 2-ethyl hexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachyl alcohol, gadoleyl alcohol, behenyl alcohol, erucyl alcohol and brassidyl alcohol and the technical mixtures thereof obtained, for example, in the high-pressure hydrogenation of technical methyl esters based on fats and oils. R is preferably derived from alcohols containing 8 to 14 carbon atoms and more preferably from technical mixtures of such alcohols. In one particular embodiment, R is derived from technical mixtures of octanol so that the alkyl groups R in formula (I) have in particular the following composition:

0 to 10% by weight $C_6$ alkyl groups,
50 to 100% by weight $C_8$ alkyl groups,
0 to 10% by weight $C_{10}$ alkyl groups,
0 to 10% by weight $C_{12}$ alkyl groups,
0 to 10% by weight $C_{14}$ alkyl groups,
0 to 10% by weight $C_{16}$ alkyl groups,
0 to 10% by weight $C_{18}$ alkyl groups.

The present invention also relates to a process for the production of substantially odorless granules of alkyl sulfates corresponding to formula (I) with a content of unsulfonated components of less than 0.2% by weight, based on active substance content, characterized in that water-containing pastes of alkyl sulfates with a content of unsulfonated components of more than 0.3% by weight are granulated and, at the same time, dried in a fluidized bed, optionally in the presence of carrier materials.

DETAILED DESCRIPTION OF THE INVENTION

In the context of the present invention, the expression "active substance content" means the content of detersive alkyl sulfate as determined by the Epton method.

Conventional water-containing alkyl sulfate pastes obtained after sulfation of the corresponding alcohols and subsequent neutralization are used in the process according to the invention. Since the sulfation is not complete, above all in industrial plants, and yields partly unidentified secondary products without any sulfate groups, conventional alkyl sulfate pastes also always contain so-called "unsulfonated components". These unsulfonated components are understood to be both the unreacted alcohols and the secondary products. The water-containing alkyl sulfate pastes normally contain the unsulfonated components in quantities of more than 3% by weight and generally between 0.5 and 2.5% by weight, based on active substance content. For example, water-containing technical octyl sulfate pastes contain between 0.5 and 2.5% by weight of unsulfonated components and 35 to 65% by weight and preferably 35 to 45% by weight of technical octyl sulfates with the chain distribution shown above for the technical octyl moiety and—in small quantities of generally below 3% by weight—alkali metal salts, such as sodium chloride and/or sodium sulfate. The balance of the pastes to 100% by weight is water.

These conventional alkyl sulfate pastes may be granulated and, at the same time, dried in the fluidized bed either on their own or in the presence of solid carrier materials. In the fluidized bed, the water evaporates from the paste, leaving partly to fully dried "nuclei" which are coated with more water-containing paste introduced or with the carrier materials added, granulated and, again, simultaneously dried.

In the most simple case, they are granulated and, at the same time, dried in the fluidized bed on their own. In this case, the water-containing pastes are introduced simultaneously or successively through one or more nozzles. If carrier materials are to be added, they are introduced at the same time as, but separately from, the water-containing pastes, preferably through an automatically controlled solids metering system.

Preferred fluidized beds have circular base plates (diffusor plates) between 0.4 and 5 m in diameter, for example 1.2 m or 2.5 m in diameter. The base plate may be a perforated plate, a Conidur plate (a product of Hein & Lehmann, Federal Republic of Germany) or a perforated plate of which the perforations (throughflow openings) are covered by a gauze with mesh widths smaller than 600 µm. The gauze may be arranged in or above the throughflow openings. However, the gauze is preferably located immediately below the throughflow openings of the diffusor plate. This is preferably done by sintering on a metal gauze with the appropriate mesh width. The metal gauze preferably consists of the same material as the diffusor plate, more particularly stainless steel. The mesh width of the gauze mentioned is preferably between 200 and 400 µm.

According to the invention, the process is preferably carried out at fluidizing air flow rates of 1 to 8 m/s and, more particularly, 1.5 to 5.5 m/s. The granules are preferably discharged via a grading stage. Grading is preferably carried out by a stream of drying air flowing in countercurrent (grading air) which is controlled in such a way that only particles beyond a certain particle size are removed from the fluidized bed while smaller particles are retained therein. In one preferred embodiment, the inflowing air is made up of the heated or unheated grading air and the heated bottom air. The bottom air temperature is preferably between 80 and 400° C. The fluidizing air cools through heat losses and through the heat of evaporation, its temperature—as measured preferably about 5 cm above the base plate —being in the range from 60 to 120° C., preferably in the range from 65 to 90° C. and more preferably in the range from 70 to 85° C. The air exit temperature is preferably between 60 and 120° C. and more particularly below 80° C. Other advantageous embodiments of the process according to the invention can be found in hitherto unpublished German patent application 197 50 424.8 and in the above-cited European patent EP-B-603 207.

In the preferred fluidized bed process, a starting material acting as an initial carrier for the surfactant paste sprayed in must be present at the start of the process. Suitable starting materials are the alkyl sulfate granules themselves (optionally containing carrier materials) which have been obtained in a preceding process run. Alternatively, the carrier materials may be used as the starting material. In one particular embodiment, alkyl sulfate granules with a particle size above 0.2 and below 0.9 mm are used as the starting material and are preferably introduced via a roll mill.

In cases where carrier materials are incorporated, they are preferably inorganic carrier materials and, more particularly, alkali metal carbonates, alkali metal sulfates, crystalline or amorphous alkali metal silicates, crystalline or amorphous layer silicates and/or zeolites. The ratio by weight of carrier material to alkyl sulfate is not critical and may be between 0:100 and 50:50 and is preferably up to 20:80.

The granules obtained from the fluidized bed are then preferably cooled in a separate fluidized bed and graded by means of a sieve into granules between 0.9 and 5 mm in size as the "accepts" fraction, into granules over 5 mm in size as the oversize fraction and into granules under 0.9 mm in size as the undersize fraction. The granules of the undersize fraction are returned to the fluidized bed. The oversize fraction is ground, preferably to a particle size below 0.9 mm, and returned to the fluidized bed.

In the context of the present invention, the surfactant granules are regarded as dried if the free water content is below 10% by weight and preferably between 0.1 and 2% by weight, based on the final granules.

It is crucial to the process according to the invention that the granules remain in the fluidized bed until the content of unsulfonated components is below 0.2% by weight, based on active substance. The process is preferably carried out until the content of unsulfonated components is between 0.08 and 0.15% by weight, based on active substance. Under the above conditions, this is generally achieved after a residence time of the granules in the fluidized bed of 1 to 5 hours and preferably 1.5 to 3 hours. How the content of unsulfonated components is reduced has not yet been fully elucidated. However, applicants assume that unsulfonated components are "entranced" and thus removed from the granules by the fluidized bed drying step.

Granules of high bulk density are obtained by the process according to the invention. The active substance content varies according to the quantity of carrier materials added and, in one particular embodiment, is more than 80% by weight and preferably between 85 and 95% by weight.

The alkyl sulfate granules obtained by the process according to the invention are substantially odorless both as granules and in the form of an aqueous solution, i.e. after dissolution of the granules in water. The odor is distinctly less strong than that of the alkyl sulfate pastes used and is also weaker than that of spray-dried powders. In addition, the alkyl sulfate granules are dust-free and free-flowing and non-tacky or subsantially non-tacky so that they are easy to handle in "big bags".

The present invention also relates to the use of the granules of alkyl sulfates corresponding to formula (I) produced in accordance with the invention as surfactants for the production of laundry detergents, dishwashing detergents and cleaners. The granules according to the invention may be present in the laundry detergents, dishwashing detergents and cleaners in the usual quantities and preferably in quantities of 0.1 to 30% by weight, based on the particular composition.

The present invention also relates to the use of the granules of alkyl sulfates corresponding to formula (I) produced in accordance with the invention as surfactants for the production of cleansing cosmetics for the hair and skin, more particularly for the production of hair shampoos, shower baths, wash lotions and the like. The granules according to the invention may be present in products such as these in quantities of 0.1 to 30% by weight, based on the particular product.

EXAMPLES

I. Materials Used

A1) Octanol sulfate, sodium salt, in the form of a 43.9% by weight water-containing paste of octanol sulfate. Characteristics: chain distribution: 0–2% by weight $C_6$, 93–100% by weight $C_8$, 0–5% by weight $C_{10}$; unsulfonated component 1.0% by weight, based on 43.9% by weight active substance content; sodium sulfate 0.5% by weight; sodium chloride 0.1% by weight.

II. Production of the Granules in a Fluidized Bed

The water-containing paste A1) was sprayed into a fluidized bed.

Process parameters:
- Inflowing air: 17,000 to 20,000 Nm/h
- Inflowing air temperature: 170° C.
- Air exit temperature: 68–71° C.
- Quantity sprayed: 1,000–1,200 kg/h
- Fluidized bed differential pressure: >30 mbar
- Test duration: 15 h
- Quantity of product: 6.5 t
- Mean residence time: 1.7 hours Octanol sulfate granules with the following characteristics were obtained:
- Bulk density: 710–740 g/l
- Active substance content: 88–95 g/l
- Chain distribution: 0–2% by weight $C_6$, 93–100% by weight $C_8$, 0–5% by weight $C_{10}$
- Unsulfonated component: 0.17% by weight, based on active substance content
- Odor: faint

III. Odor

5% by weight aqueous solutions were prepared from
- paste A1)
- powder obtained by spray drying of paste A1)
- granules according to the invention.

Subjective comparison of the odor revealed a very strong odor for the paste, a distinct odor for the spray-dried powder and a very faint odor in the case of the granules according to the invention.

What is claimed is:

1. A process for making substantially odorless granules of alkyl sulfates corresponding to formula (I):

$$R\text{—}O\text{—}SO_3X \qquad (I)$$

wherein R is an alkyl group containing from 6 to 18 carbon atoms, and X is selected from the group consisting of an alkali metal, an alkaline earth metal, ammonium, an alkyl ammonium, and alkanolammonium, and a glucammonium ion, the process comprising:
  (a) providing a water-containing paste of alkyl sulfates having a content of unsulfonated components of greater than 0.3% by weight; and
  (b) simultaneously granulating and drying, in a fluidized bed, the water-containing paste of alkyl sulfates to form substantially odorless granules of alkyl sulfates, over a period of time of from about 1 to 5 hours, and wherein the substantially odorless granules thus formed have less than 0.2% by weight, based on the weight of active substance, of unsulfonated components present therein.

2. The process of claim 1 further comprising drying the water-containing paste of alkyl sulfates in the presence of a carrier material.

3. The process of claim 1 wherein the substantially odorless granules of alkyl sulfates have an alkyl sulfate content of greater than 80% by weight, based on the weight of active substance.

4. The process of claim 2 wherein the carrier material is selected from the group consisting of alkali metal carbonates, alkali metal sulfates, crystalline alkali metal silicates, amorphous alkali metal silicates, layer silicates, zeolites, and mixtures thereof.

5. The product of the process of claim 1.

6. The product of the process of claim 2.

7. The product of the process of claim 3.

8. The product of the process of claim 4.

9. A cleaning composition containing from 0.1 to 30% by weight, based on the weight of the composition, of the substantially odorless granules of alkyl sulfates of claim 1.

* * * * *